(12) United States Patent
Geelen et al.

(10) Patent No.: US 11,272,902 B2
(45) Date of Patent: Mar. 15, 2022

(54) ULTRASOUND PROBE HOLDER ARRANGEMENT USING GUIDING SURFACES AND PATTERN RECOGNITION

(71) Applicant: KONINKLIJKE PHILIPS N.V., Eindhoven (NL)

(72) Inventors: Paul Jean Geelen, Eindhoven (NL); Mart Kornelis-Jan Te Velde, Helmond (NL); Franciscus Hendrikus van Heesch, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 181 days.

(21) Appl. No.: 16/490,314

(22) PCT Filed: Mar. 1, 2018

(86) PCT No.: PCT/EP2018/055050
§ 371 (c)(1),
(2) Date: Aug. 30, 2019

(87) PCT Pub. No.: WO2018/158369
PCT Pub. Date: Sep. 7, 2018

(65) Prior Publication Data
US 2020/0015780 A1    Jan. 16, 2020

(30) Foreign Application Priority Data
Mar. 1, 2017    (EP) .................................... 17158732

(51) Int. Cl.
*A61B 8/00*    (2006.01)
(52) U.S. Cl.
CPC .......... *A61B 8/4209* (2013.01); *A61B 8/4263* (2013.01)

(58) Field of Classification Search
CPC ........................... A61B 8/4209; A61B 8/4263
See application file for complete search history.

(56) References Cited

U.S. PATENT DOCUMENTS

| 4,483,344 A | 11/1984 | Atkov et al. |
| 5,094,243 A | 3/1992 | Puy et al. |

(Continued)

FOREIGN PATENT DOCUMENTS

| DE | 4131430 A1 | 3/1993 |
| JP | 2008036046 A | 2/2008 |

(Continued)

OTHER PUBLICATIONS

International Search Report for International Application No. PCT/EP2018/055050, filed Mar. 1, 2018, 4 pages.

(Continued)

*Primary Examiner* — Bill Thomson
*Assistant Examiner* — Delia M. Appiah Mensah (57) ABSTRACT

An ultrasound probe arrangement comprises a holder for application to a surface, a housing mounted over the holder and a probe carrier. The housing has an inner guide surface which comprises a portion of a sphere and the probe carrier comprises a disc having an outer guide surface around the outer rim of the disc which comprises a portion of sphere. The probe carrier is slidable within the housing with the inner and outer guide surfaces in contact. An ultrasound probe is carried by the probe carrier and makes contact with the surface, e.g. skin. This arrangement enables the probe to be held in a desired orientation so that a clinician can work hands-free. The disc design enables different probe designs to be used with the same basic holder and housing design.

16 Claims, 6 Drawing Sheets

(56) References Cited

U.S. PATENT DOCUMENTS

| | | | |
|---|---|---|---|
| 5,598,845 A | | 2/1997 | Chandraratna et al. |
| 6,261,231 B1* | | 7/2001 | Damphousse ....... A61B 8/4209 600/437 |
| 6,338,716 B1* | | 1/2002 | Hossack ............. A61B 8/0833 600/459 |
| 7,846,103 B2 | | 12/2010 | Cannon, Jr. et al. |
| 8,876,720 B2 | | 11/2014 | Vezina |
| 9,474,505 B2 | | 10/2016 | Banjanin et al. |
| 10,973,493 B2* | | 4/2021 | Kim ........................ A61B 8/00 |
| 2011/0251489 A1* | | 10/2011 | Zhang ................. A61B 8/4227 600/459 |
| 2015/0297176 A1 | | 10/2015 | Rincker et al. |
| 2016/0113724 A1 | | 4/2016 | Stolka et al. |
| 2016/0328998 A1 | | 11/2016 | Pedersen et al. |

FOREIGN PATENT DOCUMENTS

| | | | | |
|---|---|---|---|---|
| WO | 2015075603 A1 | | 5/2015 | |
| WO | WO-2016201006 A1 * | | 12/2016 | ............... A61B 8/58 |

OTHER PUBLICATIONS

Written Opinion of the International Searching Authority for International Application No. PCT/EP2018/055050, filed Mar. 1, 2018, 6 pages.

Jong, R., "Essentials of Sonography and Patient Care", 3rd Edition, published May 17, 2012, 4 pages (Abstract).

Hill, et al., "Medical image registration". Physics in Medicine and Biology, 46 (2001), pp. R1-R45.

Arbona, et al., "Ultrasound-Guided Regional Anesthesia: A Practical Approach to Peripheral Nerve Blocks and Perineural Catheters", Cambridge Medicine (Hardcover), 1st Edition, 1 page (Abstiact).

* cited by examiner

ULTRASOUND PROBE HOLDER ARRANGEMENT USING GUIDING SURFACES AND PATTERN RECOGNITION

RELATED APPLICATIONS

This application is the U.S. National Phase application under 35 U.S.C. § 371 of International Application No. PCT/EP2018/055050, filed on Mar. 1, 2018, which claims the benefit of European Application No. 17158732.2, filed Mar. 1, 2017. This application is hereby incorporated by reference herein.

FIELD OF THE INVENTION

This invention relates to an ultrasound probe arrangement, in particular an ultrasound probe and a positioning system which enables the position of the probe to be adjusted relative to a surface to which the probe is being applied.

BACKGROUND OF THE INVENTION

Ultrasound probes can be used for imaging or other monitoring procedures, for example during minimally invasive cardiac interventions.

Ultrasound may be used during minimal invasive interventions in the heart, for example during heart valve repairs. This type of procedure is time consuming and it is important to have a stable image of the relevant part of the patient's body for a long period of time. Clinicians typically have to control the probes manually, for example passing the probe over the surface of the body by hand.

With regard to such a manual process, some applications use X-ray imaging/radiation together with ultrasound imaging. By holding the probe manually, the hand of the clinician is exposed to the harmful X-ray radiation. During long-term procedures, holding the ultrasound probe in a steady position is also difficult and strenuous for the clinician.

It is also known during ultrasound-guided procedures to make use of a probe positioning device, which holds the ultrasonic probe. The probe positioning device holds the probe at a predetermined position relative to the patient. The operation of these systems varies from completely manual, to completely automated.

In an automated probe positioning system, a control system corrects for the movement of the patient or disturbances in the environment. These systems can use a tilt, pressure or other sensor carried by the probe to collect positional data. The positioning system, such as a robotic arm, is coupled to the probe. The positioning system can provide roll and pitch control as well as translating the probe in lateral and longitudinal directions. A processor receives signals from the sensors corresponding to the actual orientation of the probe and controls the positioning system to adjust the orientation of the probe until the desired position is achieved.

This approach enables recording of the position of the ultrasound probe, for example so that the spatial relationship between multiple images can be derived. However, lower cost probe positioning systems which are not fully automated do not do not provide a convenient way of recording position information.

The use of a probe positioning system gives a more stabilized control compared to a hand held approach, giving reduced image distortion.

The current methods, whether fully manual or fully automated, are costly, take up valuable space around the patient, and in some circumstances may still lead to difficulties in providing a stable image. A steady image is particularly important for ultrasound-guided procedures.

U.S. Pat. No. 5,598,845 discloses a transducer device in which the transducer is mounted inside a spherical enclosure, and the spherical enclosure fits within a ring which is attached to the skin. This enables adjustment of the orientation of the transducer. The spherical enclosure has to be designed specifically for the ultrasound probe, which is attached to the inside walls of the enclosure.

SUMMARY OF THE INVENTION

The invention is defined by the claims.

According to examples, there is provided an ultrasound probe arrangement, comprising:
 a holder for application to a surface;
 a housing mounted over the holder, the housing having an inner guide surface which comprises a portion of a sphere;
 a probe carrier comprising a disc having an outer guide surface around the outer rim of the disc which comprises a portion of sphere, wherein the probe carrier is slidable within the housing with the inner and outer guide surfaces in contact; and
 an ultrasound probe can be carried by the probe carrier and which projects below the probe carrier towards the surface for making direct contact with the surface.

In particular, in accordance with examples in accordance with a first aspect of the invention, there is provided an ultrasound probe arrangement, comprising:
 a holder (10) for application to a surface;
 a housing (14) mounted over the holder, the housing having an inner guide surface (16) which comprises a portion of a sphere;
 a probe carrier (18) comprising a disc having an outer guide surface around the outer rim of the disc which comprises a portion of a sphere, wherein the probe carrier (18) is slidable within the housing (14) with the inner and outer guide surfaces in sliding contact, wherein
 the arrangement is configured such that a probe may be mounted in the carrier in a position such that a point of rotation of the probe caused by sliding of the probe carrier within the housing corresponds to a point of contact of a tip of the probe with the surface.

The holder, housing and probe carrier together function as a positioning system. They enable the probe to be held in a desired orientation so that a clinician can work hands-free. This means that blocking of X-ray imaging/radiation equipment around the patient is avoided. A small form factor also means there is also less blocking of other medical equipment around the patient. An additional benefit of the present invention is that an ultrasound transducer array, which is housed within the probe's tip, is arranged to be in a secured contact with the surface of the patient's body. This permits the transducer array to assure an efficient ultrasound wave transmission into and from the body.

The disc is designed for a specific probe design. By projecting the probe below the disc (by which is meant towards the surface compared to the disc) it may make direct contact with the skin. This means that a single contact point with the skin may be maintained during adjustment of the probe position.

The positioning system as a whole enables easy and intuitive use. By using a positioning system, the ultrasound probe is more stabilized compared to the situation where it is held by hand. Hence, the positioning system results in reduced image distortion. The holder can be sterilized before it is applied to the surface. For some applications, a hand held ultrasound probe was previously considered impractical because of the invasion of the sterile field by the hand of the sonographer. Multiple ultrasound probes can be placed on the surface by using several positioning systems. This does not require more operators as would be the case for hand held ultrasound probes.

The overall positioning system is attached to the surface and is not connected to the fixed world. This reduces the distortions that can act on the ultrasound probe and hence on the resulting images. For example, the positioning system will move in the same manner as the movements of the patient.

The arrangement provides easy fixation of orientation angles: once the desired orientation is achieved by the clinician (sonographer), the probe orientation is maintained after the clinician's hand is released, as a result of the friction between the two guide surfaces. For example, no screw tightening is needed.

The arrangement can be used with a miniaturized probe to reduce the overall size and hence become less obtrusive.

The housing may comprise a disc, the disc having said inner guide surface which comprises a portion of a sphere, i.e. the housing may be in the form of a disc. The disc may be a generally cylindrical or tubular-shape disc.

By providing the housing in the form of a disc, a particularly compact and flat arrangement is provided which is convenient when performing ultrasound examination.

The outer guide surface around the outer rim of the disc preferably comprises a portion of a sphere shaped to engage flush with the inner guide surface.

The inner guide surface preferably comprises a continuous portion of a sphere.

The arrangement is configured such that a probe may be mounted in the carrier in a position such that a point of rotation of the probe corresponds to a point of contact of a tip of the probe with the surface. The point of rotation means a center of rotation of the probe; the point about which the probe rotates by means of sliding within the housing. By making the center of rotation a point of contact with the surface, the angular orientation of the probe relative to the surface can be varied without translating the probe (namely transducer array) across the surface, which can introduce motion distortions in generated imagery and measurements.

The probe is preferably positioned to make contact with the surface at a location corresponding to the center of the sphere. This is one means of ensuring that the point of rotation corresponds to the location of the tip of the probe against the surface.

This central location does not shift laterally in response to adjustment of the probe orientation angle, so that the position on the surface remains constant during adjustment.

Existing probe holders do not have the rotation point of the probe on the skin. This introduces a translation when re-adjusting the probe rotation.

The center of the sphere may mean the center of the sphere of which the inner guide surface is a portion or the sphere of which the outer guide surface is a portion. Since the two surfaces preferably engage flush with one another, these two spheres may be considered one and the same.

The outer guide surface is a surface around the outer rim of a disc. This arrangement provides superior maneuverability and control compared other arrangements. In particular, a large degree of rotational freedom is possible and the arrangement also allows the carrier to be held fixed in any orientational position merely through frictional contact with the housing surface which occurs upon pressing of the probe against the skin.

The outer guide surface around the outer rim of the disc may in particular be a radially outermost surface of the outer rim of the disc.

The portion of a sphere of the inner guide surface may be a spherical segment, i.e. the inner guide surface may comprise a portion of a sphere in the form of a spherical segment.

Spherical segment is a geometric term. It means the solid defined by cutting a sphere with a pair of parallel planes. It can be thought of as a spherical cap with the top truncated; it corresponds to a spherical frustum.

By providing the inner guide surface as a spherical segment, with the carrier comprising a disk shaped to engage slidingly with the inner surface of said segment, there is provided two dimensions of rotational freedom for the carrier, with the central annulus of the spherical segment providing an access point via which the carrier can be so rotationally manipulated.

Where the inner guide surface comprises a spherical segment, the portion of a sphere of the outer guide surface may be a spherical sub-segment of said spherical segment, i.e. a spherical segment forming a portion of said spherical segment of the inner guide surface. This ensures a large degree of rotational freedom in two dimensions about the inner surface of the housing.

The housing preferably has an adjustable position in the holder. This adjustable position enables a pressing force to be adjusted. This is for example needed for cardiac ultrasound to enable good probe positioning between the ribs.

The holder and the housing may together form a ratchet arrangement. In this way, the housing can be pushed into the holder (i.e. towards the surface), until a desired position is reached. This desired position corresponds to a particular pressing force, in that the surface provides a reaction force which depends on the amount of depression. The housing is then held in position by the ratchet arrangement. The ratchet arrangement can be released to subsequently decouple the housing and holder.

The adjustable position may comprise a set of discrete positions, wherein each discrete position allows for a limited amount of relative movement between the holder and the housing. In this way, there is some normal (i.e. perpendicular to the surface) movement allowed. When adjusting the probe carrier and probe orientation, the lateral contact position is preferably fixed but the height will vary. The allowed relative movement takes up this height variation.

The arrangement may further comprise an adhesive component for attaching the holder to the surface. In this way, the holder may be fixed in position before applying the probe.

The arrangement may further comprise a position sensor arrangement for sensing the relative position of the housing and the probe carrier.

In this way, the positioning system can track the orientation angles of the ultrasound probe. This information can be used for distortion detection and image registration.

The position sensor arrangement for example comprises a light source and a light detector provided at one of the housing and the probe carrier, and a detectable image on the other of the probe carrier and the housing. By reading the image (by monitoring reflected light), a local image portion may be recognized and identified, and this local portion encodes location information. Alternative positioning systems are possible such as gyroscopes and/or acceleration sensors and/or magnetic sensors.

The image may for example comprise a dot pattern, wherein the local dot pattern at any location of the image identifies that location. This provides a positioning system which is simple to implement.

The image may be provided on the inner guide surface and the light source and light detector are provided on the probe carrier.

The arrangement is preferably an ultrasound imaging probe.

Examples in accordance with another aspect of the invention provide a method of adjusting the positon of an ultrasound probe, comprising:

applying a holder (10) to a surface;

mounting a housing (14) over the holder, the housing having an inner guide surface (16) which comprises a portion of a sphere;

supporting an ultrasound probe (24) on a probe carrier (18) comprising a disc having an outer guide surface which comprises a portion of sphere, wherein the probe carrier is slidable within the housing with the inner and outer guide surfaces in sliding contact, wherein the ultrasound probe (24) projects below the probe carrier to make direct contact with the surface, and wherein the probe carrier and housing are configured such a point of rotation of the probe caused by sliding of the probe carrier within the housing corresponds to a point of contact of a tip of the probe with the surface; and adjusting the position of the ultrasound probe by moving the probe carrier within the housing, wherein the probe projects from the probe carrier towards the surface.

The position of the holder over the housing may also be adjusted.

The method may further comprise making contact between the ultrasound probe and the surface at a location corresponding to the center of the sphere.

BRIEF DESCRIPTION OF THE DRAWINGS

Examples of the invention will now be described in detail with reference to the accompanying drawings, in which.

DETAILED DESCRIPTION OF EMBODIMENTS

The invention provides an ultrasound probe arrangement which comprises a holder for application to a surface, a housing mounted over the holder and a probe carrier. The housing has an inner guide surface which comprises a portion of a sphere and the probe carrier comprises a disc having an outer guide surface around the outer rim of the disc which comprises a portion of sphere. The probe carrier is slidable within the housing with the inner and outer guide surfaces in contact. An ultrasound probe may be carried by the probe carrier and make contact with the surface, e.g., the skin.

This arrangement enables the ultrasound probe to be held in a desired orientation so that a clinician can work hands-free. The disc design enables different probe designs to be used with the same basic holder and housing design.

Figure 1:
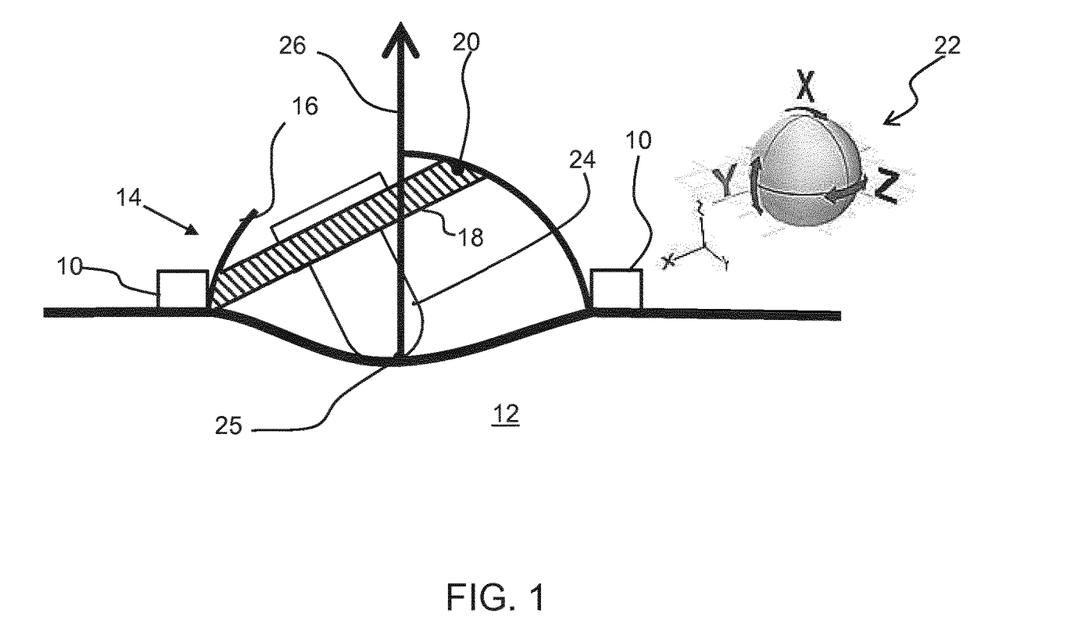
FIG. 1 shows in schematic form the general components of the ultrasound probe arrangement.

FIG. 1 shows in schematic form the general components of the ultrasound probe arrangement.

The arrangement comprises a holder 10 to be attached to the surface 12 to be imaged, typically the skin. It is the part that holds the whole probe arrangement to the surface. It is attached by an adhesive. Thus, the holder is wearable and it enables the probe to used hands-free. The holder can be a disposable item for hygiene reasons. The shape is designed having regard to the particular surface, in particular the specific part of the body to which the probe arrangement is to be attached.

The holder 10 receives a housing 14 which has an inner guide surface 16 which comprises a portion of a sphere.

A probe carrier 18 forms a disc having an outer guide surface 20 around the outer rim of the disc which also comprises a portion of sphere. The sphere of the outer guide surface has essentially the same (and in practice slightly smaller) radius as the sphere of the inner guide surface. The probe carrier 18 is slidable within the housing with the inner and outer guide surfaces in contact. This gives three rotational degrees of freedom (a sphere rotating within a sphere) as shown by the image 22. The holder 10, housing 14 and probe carrier 18 together define a positioning system.

The probe carrier is designed for a specific ultrasound probe 24. Thus, various ultrasound probes can be used by using different probe carriers, but the same housing and holder may be used. In the present embodiment the ultrasound probe 24 has a reduced form factor, such that it is arranged to be substantially enclosed in the housing 14.

This makes such probe arrangement suitable for longer term monitoring purposes, wherein the patient may wear clothes above the attached to his/her body probe arrangement.

An ultrasound probe 24 is carried by the probe carrier and it projects below the probe carrier 18 towards the surface 12 for making direct contact with the surface. FIG. 1 only shows the lower part of the probe 24. It will also have an upper part and a connecting cable to connect to remote signal analysis equipment. The probe may be connectable to the probe carrier by a snap or click connection or by any other convenient connector arrangement.

The probe typically has an acoustic lens at its outer surface, and this lens makes contact with the surface. The overall positioning system thus has an open base so that the contact characteristics between the probe and the surface are defined only by the probe design. The probe and the signal processing applied to the captured signals thus do no need to be adapted in order to take account of the design of the positioning system.

The probe 24 makes contact with the surface 12 at a location 25 beneath the housing 14 which corresponds to the center of the spherical surfaces. This location is below the bottom plane of the carrier, because in use a depression will be formed in the skin by the probe, as shown in FIG. 1. Arrow 26 shows the normal reaction force provided by the skin from this central contact location 25. This central contact point 25 of rotation on the skin, means that angular adjustment of the orientation does not change the lateral position of that contact point 25.

When the housing 14 is pressed against the skin and held in place by the holder 10, the ultrasound probe position is locked by the friction between the spherical surfaces 16, 20.

Figure 2:
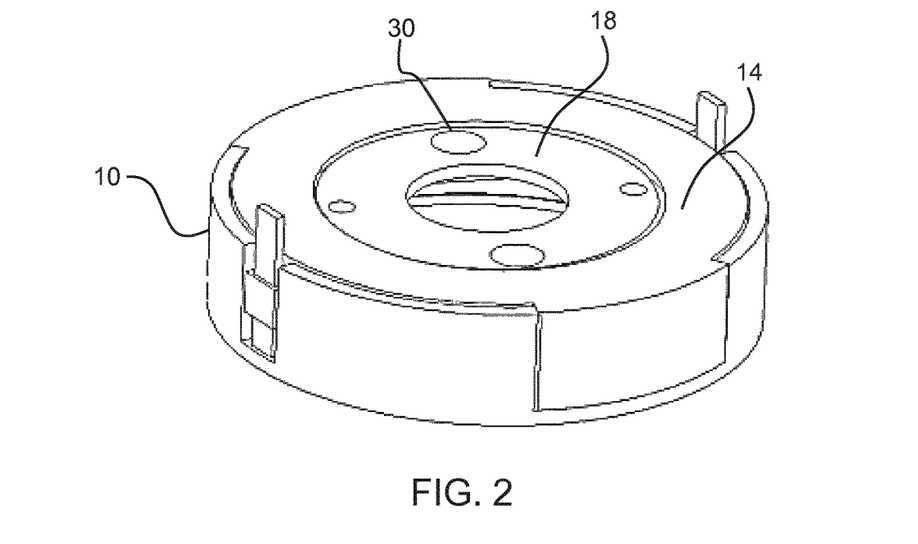
FIG. 2 shows a perspective view of a more detailed example of the positioning system.

FIG. 2 shows a perspective view of a more detailed example of the positioning system. The overall device is generally in the form of a cylindrical disc, although any other outer shape is possible. The probe carrier 18 has mounting holes 30 or other fixation features by which it connects to the probe or to an adjustment handle, which is not shown in FIG. 2.

Figure 3:
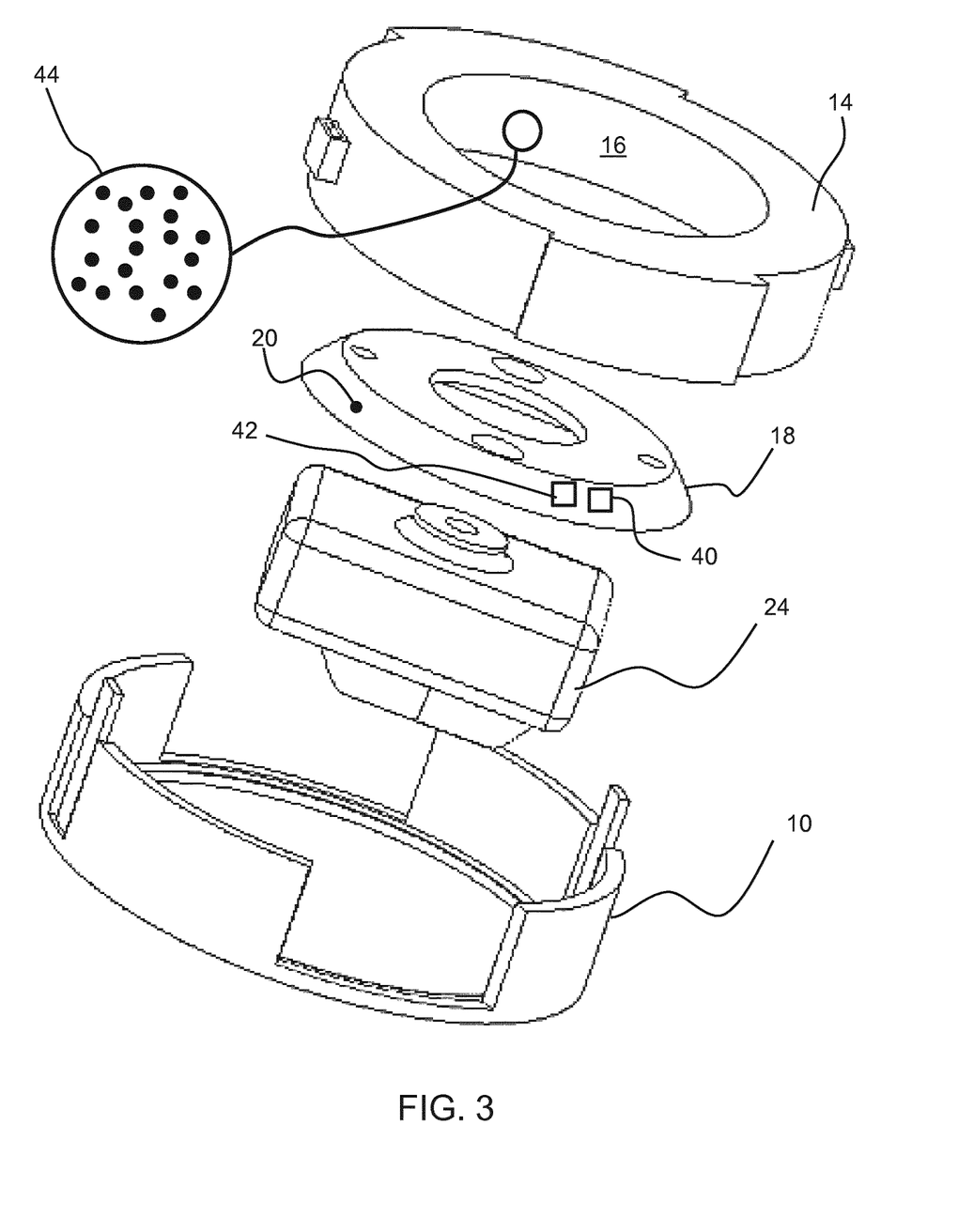
FIG. 3 shows an exploded perspective view of the components of FIG. 2 and also shows the probe.

FIG. 3 shows an exploded perspective view of the components of FIG. 2 and also shows the lower internal part of the probe 24.

FIG. 3 also shows a position sensor arrangement for sensing the relative position between the holder 18 and the housing 14. The positioning system is used to track the orientation angles of the ultrasound probe. This information can be used for distortion detection and image registration.

The position sensor arrangement comprises a light source 40 and a light detector 42 provided on the probe carrier 18 (recessed beneath the spherical outer surface 20). The light source is for example an infrared LED and the light detector is an infrared detector. This provides image recognition based on reflection from an image which is provided on the other of the holder and the housing. A portion 44 of an image is shown as a dot pattern, and the image is provided at all locations of the spherical inner guide surface 16 which may align in use with the image sensor.

By reading the image, a local image portion is recognized, and this local portion encodes location information. The use of a dot pattern for position recognition (e.g. of a pen over a page) is known. For example, the dot pattern may deviate locally from a regular grid, (as projected onto the spherical surface by a suitable transformation) and at all locations the deviation from a regular grid is different. This or any other image based position detection system may be used.

Alternative position sensor systems are possible such as gyroscopes and/or acceleration sensors.

In this example, the image is provided on the inner guide surface 16 and the light source and light detector are provided on the probe carrier 18, but they may be the other way around. The position sensing system is used to determine the three rotation angles (see FIG. 1) of the ultrasound probe.

The probe design may be optimized to fit into a housing 14 and holder 10 with the smallest possible dimensions.

The different adjustments that may be made are shown in FIGS. 4 to 7.

Figure 4:
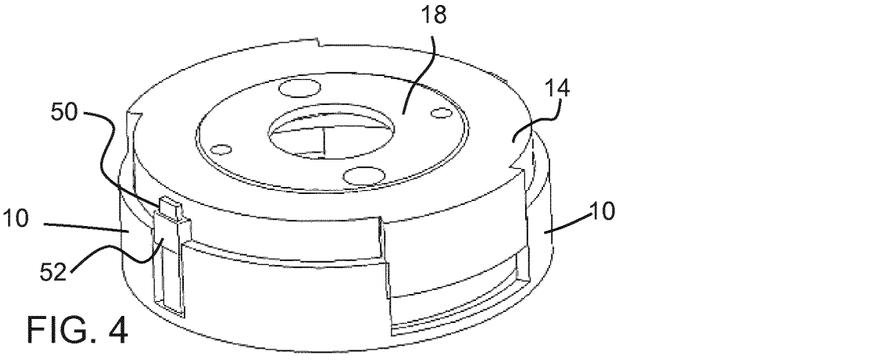
FIG. 4 shows initial fitting of the housing to the holder.

FIG. 4 shows initial fitting of the housing 14 to the holder 10.

The housing 14 has an adjustable position within the holder 10. In the example shown, the holder 10 has a set of fingers 50 which are received in openings 52 of the housing. Together they from a ratchet system so that when the housing 14 is pushed down into the holder 10 (thereby bringing the probe closer to the skin), the position is retained. However, since the probe is mounted to the carrier 18, the contact of the probe tip to the skin remains at the sphere center, regardless of the height adjustment. The tip of the probe comprises an ultrasound transducer array arranged to transmit ultrasound wave into the surface of the body. The height adjustment means that the probe tip (and sphere center) will be at different depths below the bottom surface of the holder 10.

Figure 5:
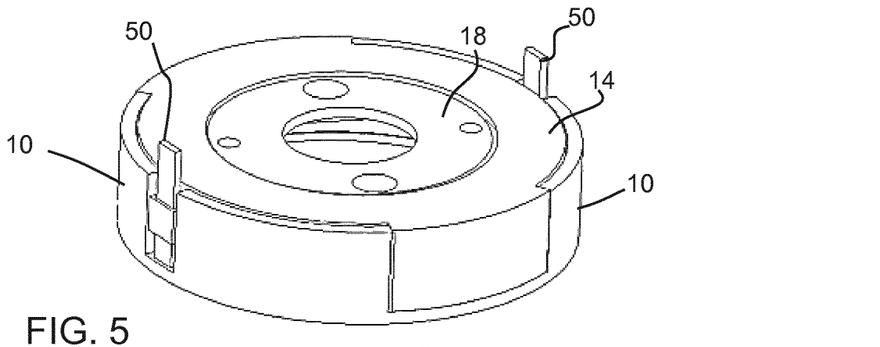
FIG. 5 shows a position with the housing further pushed down into the holder.

FIG. 5 shows a position with the housing 14 further pushed down into the holder 10.

Figure 6:
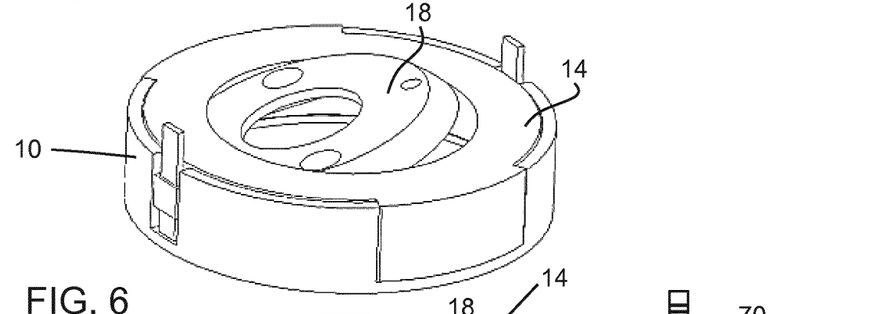
FIG. 6 shows the angular adjustment of the probe carrier.

FIG. 6 shows the angular adjustment of the probe carrier 18.

The adjustable position between the housing 14 and the holder 10 enables a pressing force to be adjusted and corresponding depth of local depression of the skin as mentioned above. This is for example needed for cardiac ultrasound to enable good probe positioning between the ribs.

Figure 7:
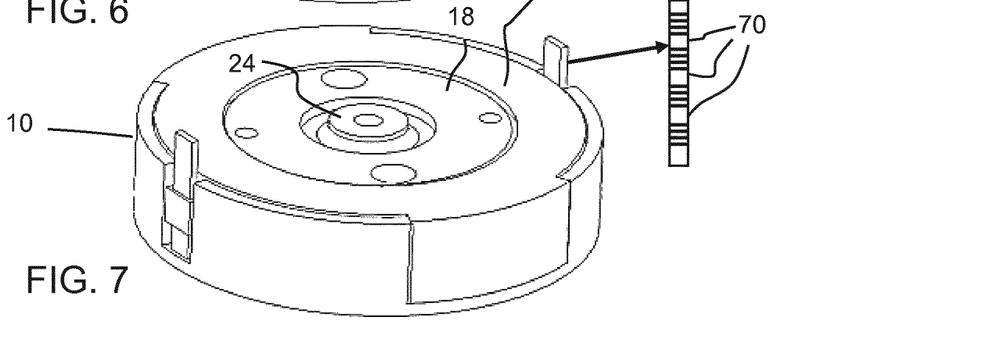
FIG. 7 shows that the adjustable position may comprise a set of discrete positions.

As shown in FIG. 7, the adjustable position may comprise a set of discrete positions 70, wherein each discrete position 70 allows for a limited amount of relative movement between the holder and the housing. The ratchet system means the discrete positions are reached in turn. FIG. 7 also shows the base part of the probe 24 attached to the carrier 18.

Figure 8:
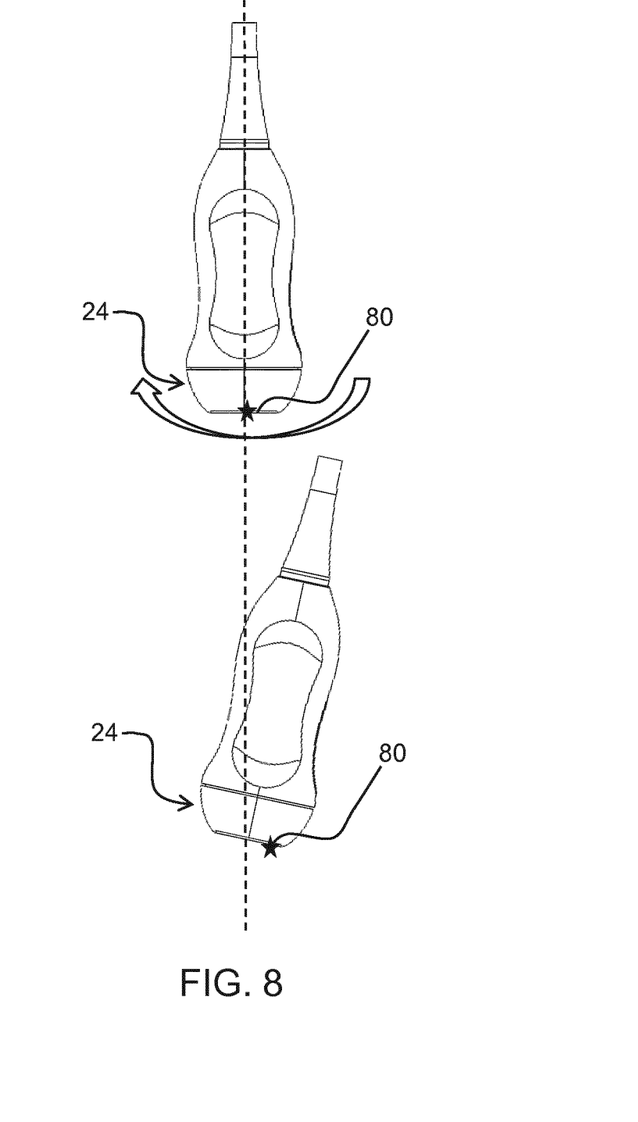
FIG. 8 shows the lower part of an ultrasound imaging probe and shows how the contact position changes during orientation adjustment.

The benefit of the set of discrete positions is explained with reference to FIG. 8, which shows an ultrasound imaging probe including the lower part 24 for mounting in the housing, as well as the top part. In the top image, the probe is oriented normally to the skin. In the lower image, the probe is rotated.

This means the lowest contact point 80 has shifted in the normal direction.

This results from a non-convex shape at the tip of the probe. The movement between the holder and the housing takes up this height difference and thereby maintains a more constant normal contact force.

A typical use of the arrangement described above will be now be explained.

The specialist first applies the lower part 24 of the ultrasound imaging probe to the probe carrier 18. Different kinds of ultrasound imaging probes can be used by using different probe carriers that can be designed for the specific probe. It shall be understood by the skilled person that the lower part of the probe 24 comprises an ultrasound transducer array (located at the probe's tip), which is arranged to transmit ultrasound waves into the body surface.

The specialist then moves the overall probe arrangement that contains the desired ultrasound probe, over the body of the patient (providing x-axis and y-axis variation to the desired location) until the desired location is reached. The specialist then fixates the probe to the skin (without removing the probe carrier).

The pressing force of the ultrasound probe on the body can be then be adjusted (z-axis variation) to ensure proper acoustic contact. This involves inserting the housing to a sufficient depth within the holder. For cardiovascular applications this feature is significant, because the ultrasound probe has to be pressed in between the ribs.

The z-axis movement is by default one-directional as explained above. The probe holder starts in the position of FIG. 4 in which the ultrasound probe presses gently against the skin. The pressing force is increased by moving the housing towards the skin. When the hand of the specialist is released the pressing force is maintained. The pressing force can be released by pressing on the openings 52 on both sides of the holder 10 to disengage the ratchet arrangement. Adjustment in both directions is then possible. This type of ratchet arrangement is well known for example as employed in a reusable tie wrap.

Many other types of mechanical locking solutions can of course be used instead.

The three rotation angles (shown in FIG. 1) around the x, y and z axes can be set by the specialist by rotating the disc in the housing. Thus, there are in total six degrees of freedom in the movement of the probe. Once the desired orientation is reached, the specialist can release his hand and the probe will maintain its orientation due to friction. By arranging the ultrasound probe to rotate around a fixed point on the skin, there are no unwanted translations when changing the orientation of the probe.

The specialist has then positioned and orientated the ultrasound probe in the desired setting and released his hand. The ultrasound imaging procedure can now start. Various procedures are possible.

The ultrasound probe may be held in a stabilized position for a long-term time. In order to detect movement of the ultrasound probe (and hence distortions) the position sensing system is used.

The ultrasound probe may instead be rotated in the housing around the three axes as part of the ultrasound procedure. The position sensing system may again be used to track the orientation angles. With this information, image registration can be carried out to stitch the images together and/or improve the image quality by overlaying and filtering techniques.

Figure 9:
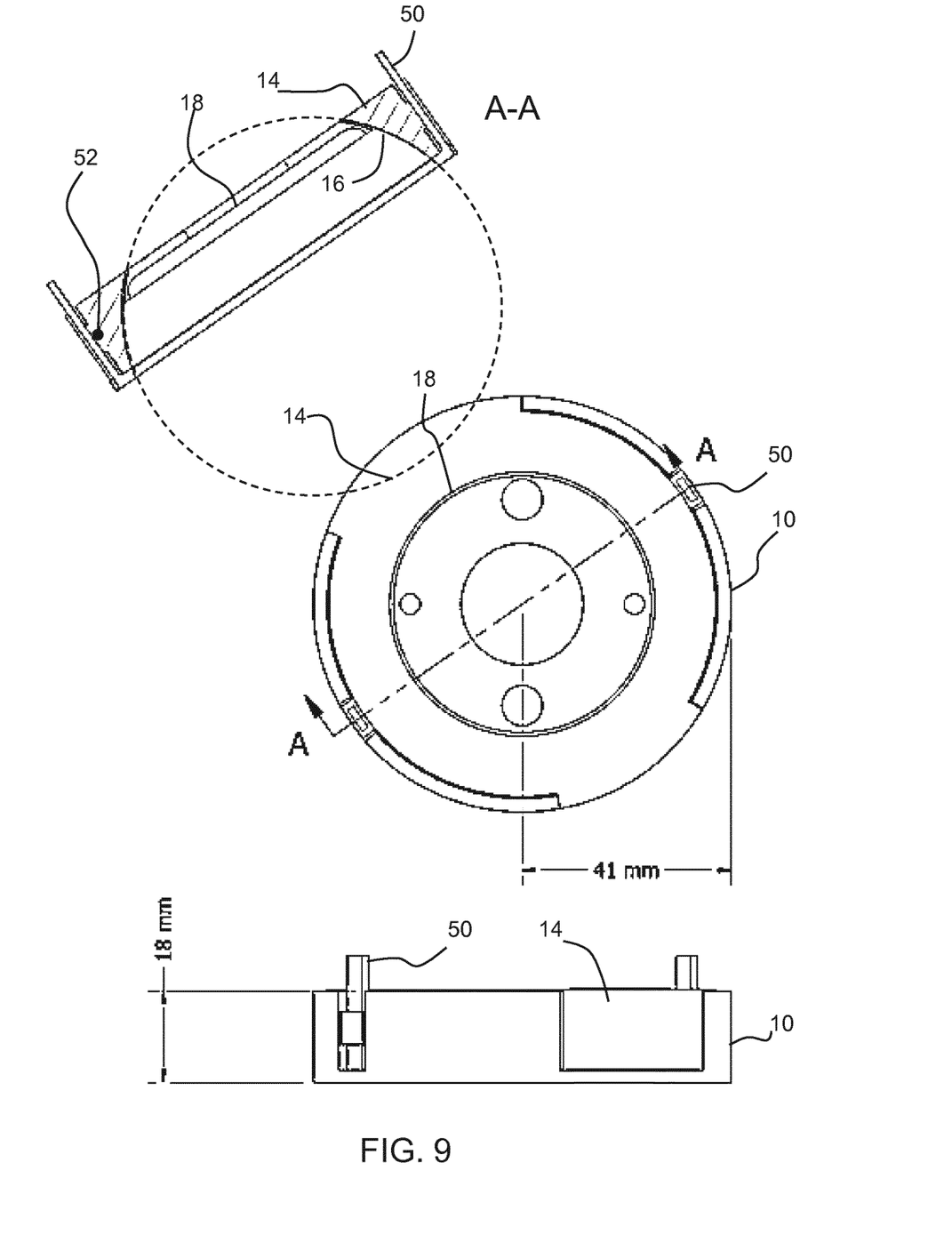
FIG. 9 shows a technical drawing of the holder and probe carrier.

FIG. 9 shows a technical drawing of the holder 10, housing 14 and probe carrier 18. It shows an example of the typical size of the arrangement; 82 mm diameter and 18 mm height in this example.

The inner guide surface 16 of the housing 14 comprises a portion of a sphere. The portion of the sphere takes the form in particular of a spherical segment, i.e. the inner guide surface comprises a portion of a sphere in the form of a spherical segment.

Spherical segment is a geometric term. It means the solid defined by cutting a sphere with a pair of parallel planes. It can be thought of as a spherical cap with the top truncated; it corresponds to a spherical frustum.

The carrier 18 comprises a disc which is received in the housing and has a rim outer guide surface shaped to engage slidingly with the inner surface of said spherical segment. This provides two dimensions of rotational freedom for the carrier. The spherical segment delineates a central annulus which provides an access point via which the carrier can be rotationally manipulated.

The outer guide surface of the carrier disk rim also comprises a portion of a sphere which is shaped co-operatively with that of the outer guide surface of the housing, so that the two are rotationally engagable. The portion of a sphere of the carrier rim outer guide surface is in particular a spherical sub-segment of said spherical segment of the housing inner guide surface. This ensures a large degree of rotational freedom in two dimensions about the inner surface of the housing.

The housing comprises a plate or disc having a thickness (height), in this example, equal to half the sphere radius (20 mm). In general, the housing has a thickness (height) in the range 30% to 70% of the sphere radius.

The probe carrier 18 is a disc, in this example with a thickness (or height) of 10% of the sphere radius and generally in the range 5% to 25% of the sphere radius. This provides a compact and flat design for the probe carrier.

The housing 14 has a top opening (annulus) just above the probe carrier 18. At certain angles of positioning, part of the probe carrier protrudes through the top opening, for example as shown in FIG. 6.

Figure 10:
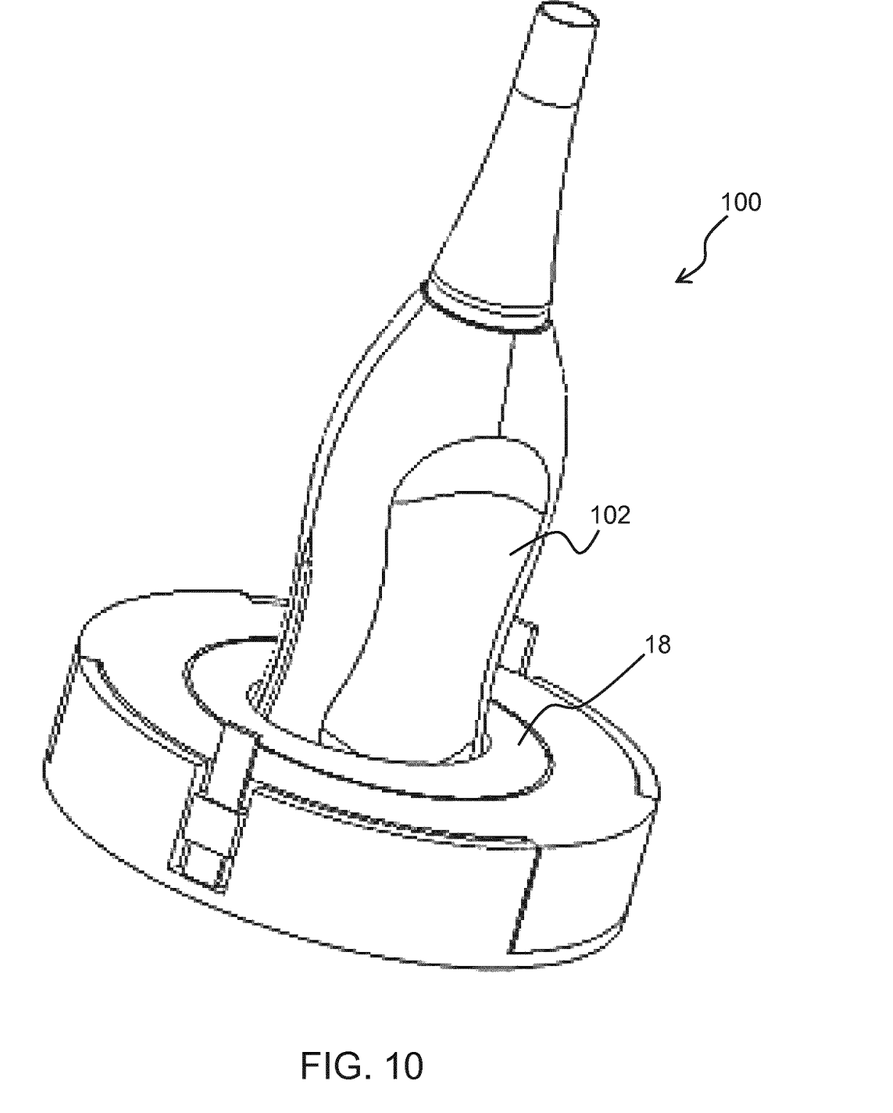
FIG. 10 shows one design of probe attached to the probe carrier.

FIG. 10 shows one design of probe 100 attached to the probe carrier 18 showing the overall probe head 102 rather than just the probe tip as in the figures above. The probe tip is not visible because it projects into the housing.

The positioning system described above provides various benefits. In addition to providing position information about images taken it may be used to aid users who are not experienced enough to execute examination protocols. The position sensing system may be used to give live feedback to the user on the orientation of the ultrasound probe. This information may then be used to guide the user through a specific examination protocol.

Some ultrasound examination protocols require that the ultrasound probe is held fixed in a certain orientation for a long-term period. The positioning system may be used to detect in real-time if the probe has unintentionally moved, and give feedback to the user.

The positioning system may be implemented at low cost, for example with a single infrared LED and camera/detector using mature technology. No active, current carrying elements are needed on the housing 14.

Orientation sensors may instead be used, for example combining data from a gyroscope, accelerometer and magnetometer. This may for example give angular accuracy around the x, y and z axes within 2 degrees. One orientation sensor may be attached to the housing, and a second to the probe carrier. By using these two sensors, the rotation angles of the disc around the x, y and z axis within in the housing are then known.

The arrangement may be used for stress echo procedures, for treatments of cardiovascular valve disease, for monitoring during angioplasty, for monitoring in intensive care units, for fine tuning of a pacemaker and for local anesthesia. The ultrasound probe may be used for imaging or other ultrasound measurements, such as blood flow measurement.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An ultrasound probe arrangement, comprising:
   a holder configured for application to a surface;
   a housing mounted over the holder, the housing having an inner guide surface which comprises a portion of a sphere;
   a probe carrier comprising a disc having:
      a planar upper surface;
      a planar lower surface parallel to the planar upper surface; and
      an outer rim extending between the planar upper surface and the planar lower surface, wherein the outer rim comprises an outer guide surface comprising a spherical segment, wherein the probe carrier is slidable within the housing with the inner and outer guide surfaces in sliding contact,
   wherein the arrangement is configured such that an ultrasound probe is mountable in the probe carrier in a position such that a point of rotation of the probe caused by sliding of the probe carrier within the housing corresponds to a point of contact of a tip of the ultrasound probe with the surface, and
   wherein the housing is receivable within the holder at an adjustable depth position within the holder such that a pressing force applied by the ultrasound probe held in use by the probe carrier against the surface is adjustable.

2. The arrangement as claimed in claim 1, wherein the housing comprises a disc having said inner guide surface.

3. The arrangement as claimed in claim 1, wherein the portion of a sphere of the inner guide surface is a spherical segment.

4. The arrangement as claimed in claim 1, wherein the spherical segment of the outer guide surface is a spherical sub-segment of said spherical segment of the inner guide surface.

5. The arrangement as claimed in claim 1, wherein the ultrasound probe is positioned in the probe carrier such that the ultrasound probe is configured to make contact with the surface at a location corresponding to the center of the sphere.

6. The arrangement as claimed in claim 1, wherein the housing has an adjustable position in the holder, wherein the holder and the housing together form a ratchet arrangement.

7. The arrangement as claimed in claim 6, wherein the adjustable position of the housing comprises a set of discrete positions, wherein each discrete position allows for a limited amount of relative movement between the holder and the housing.

8. The arrangement as claimed in claim 1, further comprising a position sensor arrangement for sensing the relative position of the housing and the probe carrier.

9. The arrangement as claimed in claim 8, wherein the position sensor arrangement comprises a light source and a light detector provided at one of the housing or the probe carrier, wherein the light detector is configured to receive a reflection of an image provided on the other of the probe carrier or the housing.

10. The arrangement as claimed in claim 9, wherein the image comprises a dot pattern with a plurality of local dot patterns at a corresponding plurality of locations of the image, wherein the light detector is configured to identify a location of the image based on the local dot pattern at the location of the image.

11. The arrangement as claimed in claim 1, further comprising the ultrasound probe carried by the probe carrier and which is arranged to project below the probe carrier towards the surface for making direct contact with the surface.

12. The arrangement as claimed in claim 11, wherein the ultrasound probe comprises an ultrasound imaging probe.

13. A method of adjusting the position of an ultrasound probe, comprising:
  applying a holder to a surface;
  mounting a housing over the holder, the housing having an inner guide surface which comprises a portion of a sphere;
  supporting an ultrasound probe on a probe carrier comprising a disc having:
    a planar upper surface;
    a planar lower surface parallel to the planar upper surface; and
    an outer rim extending between the planar upper surface and the planar lower surface, wherein the outer rim comprises an outer guide surface comprising a spherical segment, wherein the probe carrier is slidable within the housing with the inner and outer guide surfaces in sliding contact, wherein the ultrasound probe projects below the probe carrier to make direct contact with the surface, and wherein the probe carrier and housing are configured such a point of rotation of the ultrasound probe caused by sliding of the probe carrier within the housing corresponds to a point of contact of a tip of the probe with the surface, and wherein the housing is receivable within the holder at an adjustable depth position within the holder, for adjusting a pressing force applied by a probe held in use by the probe carrier against the surface; and
  adjusting the position of the ultrasound probe by moving the probe carrier within the housing, wherein the ultrasound probe projects from the probe carrier towards the surface.

14. The method as claimed in claim 13, further comprising adjusting the position of the holder over the housing.

15. The method as claimed in claim 13, comprising making contact between the ultrasound probe and the surface at a location corresponding to the center of the sphere.

16. The method as claimed in claim 13, further comprising providing an adjustable depth position within the holder, such that a pressing force applied by the ultrasound probe held in use by the probe carrier against the surface is adjustable.

* * * * *